(12) United States Patent
Larkin et al.

(10) Patent No.: US 10,317,373 B2
(45) Date of Patent: Jun. 11, 2019

(54) DIRECT FIELD ACOUSTIC TESTING IN A SEMI-REVERBERANT ENCLOSURE

(71) Applicant: MSI DFAT LLC, Baltimore, MD (US)

(72) Inventors: Paul Larkin, Mt. Airy, MD (US); Matthew Polk, Gibson Island, MD (US); Dann Hayes, Reisterstown, MD (US)

(73) Assignee: MSI DFAT LLC, Baltimore, MD (US)

( * ) Notice: Subject to any disclaimer, the term of this patent is extended or adjusted under 35 U.S.C. 154(b) by 0 days.

(21) Appl. No.: 14/435,898

(22) PCT Filed: Oct. 15, 2013

(86) PCT No.: PCT/US2013/065122
§ 371 (c)(1),
(2) Date: Apr. 15, 2015

(87) PCT Pub. No.: WO2014/062729
PCT Pub. Date: Apr. 24, 2014

(65) Prior Publication Data
US 2015/0253292 A1 Sep. 10, 2015

Related U.S. Application Data

(60) Provisional application No. 61/713,648, filed on Oct. 15, 2012.

(51) Int. Cl.
*G01N 29/30* (2006.01)
*G01N 29/04* (2006.01)
(Continued)

(52) U.S. Cl.
CPC ............. *G01N 29/30* (2013.01); *G01M 7/00* (2013.01); *G01N 29/04* (2013.01); *G01N 29/11* (2013.01);
(Continued)

(58) Field of Classification Search
CPC ........ G01N 29/30; G01N 29/04; G01N 29/11; G01N 29/46; G01N 29/22; G01M 7/00; H04R 3/12; H04R 5/02
See application file for complete search history.

(56) References Cited

U.S. PATENT DOCUMENTS 4,357,499 A * 11/1982 Bruel .................... E04B 1/8218
367/13
4,497,064 A * 1/1985 Polk ....................... H04S 1/002
381/111
(Continued)

OTHER PUBLICATIONS

Larkin et al., "Recent Developments in Direct Field Acoustic Testing", 26th Space Simulation Conference 2010: Annapolis, Maryland, USA, Oct. 18-21, 2010, pp. 465-492.

*Primary Examiner* — Helen C Kwok
(74) *Attorney, Agent, or Firm* — Medler Ferro Woodhouse & Mills PLLC

(57) ABSTRACT

An acoustic testing system includes at least four control microphones, at least four acoustic transducers, an acoustic enclosure with pre-determined reverberant characteristics which contains the at least four control microphones and the at least four acoustic transducers, a control system configured to produce a predetermined acoustic field as measured by the at least one control microphone. A unit under test is also disposed within the acoustic enclosure. Using an acoustic enclosure with pre-determined reverberant characteristics results of the increased proportion of reflected sounds in the area proximate to the unit under test such that less power is required to achieve a given acoustic test level than in a purely direct field acoustic test.

18 Claims, 5 Drawing Sheets

(51) Int. Cl.
*G01M 7/00* (2006.01)
*G01N 29/12* (2006.01)
*G01N 29/11* (2006.01)
*G01N 29/46* (2006.01)
*H04R 3/12* (2006.01)
*H04R 5/02* (2006.01)

(52) U.S. Cl.
CPC ....... *G01N 29/46* (2013.01); *G01N 2291/023* (2013.01); *G01N 2291/0289* (2013.01); *G01N 2291/105* (2013.01); *G01N 2291/2698* (2013.01); *H04R 3/12* (2013.01); *H04R 5/02* (2013.01)

(56) References Cited

U.S. PATENT DOCUMENTS

| | | | | |
|---|---|---|---|---|
| 4,989,158 A * | 1/1991 | Sloane | ................. | G01M 7/022 700/280 |
| 5,138,884 A * | 8/1992 | Bonavia | ................. | G01M 7/02 73/662 |
| 5,170,433 A * | 12/1992 | Elliott | ................. | G10K 11/1786 381/71.12 |
| 5,299,459 A * | 4/1994 | Underwood | ................. | G01M 7/022 700/280 |
| 5,638,004 A * | 6/1997 | Combs | ................. | G01R 31/024 324/539 |
| 6,031,486 A * | 2/2000 | Anderson | ................. | B64G 7/00 342/165 |
| 6,119,808 A * | 9/2000 | Steedman | ................. | E04B 1/8218 181/198 |
| 6,484,580 B2 * | 11/2002 | Eagen | ................. | G01M 7/00 73/432.1 |
| 6,591,226 B1 * | 7/2003 | Hartmann | ................. | G01M 13/028 702/183 |
| 6,668,650 B1 * | 12/2003 | Lafleur | ................. | G01M 7/00 73/571 |
| 7,123,725 B2 * | 10/2006 | Boesch, Jr. | ................. | G01N 29/036 181/155 |
| 9,109,972 B2 * | 8/2015 | Larkin | ................. | G01M 7/00 |
| 9,683,912 B2 * | 6/2017 | Larkin | ................. | G01M 7/00 |
| 2001/0032510 A1 * | 10/2001 | Eagen | ................. | G01M 7/00 73/571 |
| 2004/0024750 A1 * | 2/2004 | Ulyanov | ................. | G06N 99/002 |
| 2004/0216524 A1 * | 11/2004 | Lafleur | ................. | G01M 7/00 73/579 |
| 2010/0054496 A1 * | 3/2010 | Williams | ................. | H04R 3/02 381/93 |
| 2012/0080556 A1 * | 4/2012 | Root, Jr. | ................. | B64F 1/02 244/63 |
| 2012/0300579 A1 * | 11/2012 | Larkin | ................. | G01N 29/04 367/13 |
| 2012/0300580 A1 * | 11/2012 | Underwood | ................. | G01M 7/00 367/13 |
| 2014/0298912 A1 * | 10/2014 | Larkin | ................. | G01N 29/14 73/658 |
| 2015/0138916 A1 * | 5/2015 | Larkin | ................. | H04B 11/00 367/13 |

* cited by examiner

DIRECT FIELD ACOUSTIC TESTING IN A SEMI-REVERBERANT ENCLOSURE

CROSS-REFERENCE TO RELATED APPLICATION

The present application claims priority under 35 U.S.C. § 119(e) to U.S. provisional application No. 61/713,648 filed Oct. 15, 2012, the disclosure of which is incorporated by reference herein in its entirety.

BACKGROUND OF THE INVENTION

Field of the Invention

The present invention relates generally to the field of vibration testing of objects such as satellites, instrumentation or any other object whose reliability in operation may be evaluated using high intensity vibration testing. Specifically, the present invention relates to the application of techniques developed for direct field acoustic testing systems to the performance of vibration testing to a predetermined specification in a semi-reverberant enclosure.

Background of the Invention

The specification of co-pending U.S. application Ser. No. 13/117,870, filed May 27, 2011 titled Direct Field Acoustic Testing System and Method (hereinafter "the '870 application") is incorporated by reference herein. As discussed in the '870 application, in the field of Direct Field Acoustic Testing (DFAT) it is generally desirable to obtain an acoustic field having a uniform spectral content and low coherence throughout the space around the Unit Under Test (UUT). As demonstrated in the '870 application excellent spectral uniformity and low coherence was obtained at the control microphone locations through the use of a Multiple-Input-Multiple-Output (MIMO) arrangement incorporating multiple groups of independently controllable acoustic transducers. As discussed in U.S. Provisional Application No. 61/552,081 and International Application No. PCT/US12/62255, both titled Drive Signal Distribution for Direct Field Acoustic Testing, each of which is incorporated by reference herein in its entirety, improved spectral uniformity at non-control microphone locations was obtained by distribution of combinations of drive signals to the groups of independently controllable acoustic transducers. However, to achieve the high acoustic levels required for many spacecraft tests very large arrays of acoustic transducers and associated amplification delivering substantial electrical input power are required. Substantial cost and effort is required to transport, deploy and teardown said equipment and the high levels of input power increase the risk of failure. Additionally, it is difficult to scale down the amount of equipment required for testing small objects such as components leading to a relatively high cost for direct field acoustic testing of such smaller items. Previously attempts have been made to develop efficient methods of testing smaller objects using Single-Input-Single-Output (SISO) control architecture such as described in "Small Direct Field Acoustic Noise Test Facility" Saggini, et al. presented at the 26th Aerospace Testing Seminar. March 2011. This method utilized a large number of control microphones and a large number of acoustic sources installed on the interior walls of an enclosure. Inputs from the microphones were averaged and equalization coefficients calculated on octave bandwidths to obtain the desired acoustic spectrum. Real time adjustments were made during testing with a SISO control architecture. This method was reasonably successful in obtaining a uniform acoustic spectrum on a full octave bandwidth basis. However, as is well known to those with skill in the art the narrow band phenomena of enclosure resonances, standing waves and wave interference patterns are the greatest problem for field uniformity in an enclosure. No narrow band spectral data is given and no coherence data is given in the Saggini paper. However, as discussed in the '870 application SISO methods do not produce good narrow band uniformity and have no ability to control coherence. Accordingly, it is desirable to provide a device and method for achieving the required acoustic levels and acoustic field characteristics with less equipment, less electrical input power and in a manner that can cost efficiently accommodate acoustic testing of smaller objects.

BRIEF SUMMARY

Embodiments hereof include a direct field acoustic testing system with at least four groups of acoustical transducers contained within an acoustic enclosure offering acoustic isolation from the surrounding environment and pre-determined reverberant characteristics so as to provide an acoustic field conforming to a pre-determined specification.

Embodiments hereof also include a direct field acoustic testing system contained within an acoustic enclosure offering acoustic isolation from the surrounding environment and pre-determined reverberant characteristics with at least four microphones disposed in appropriate locations to provide at least four acoustical input signals which are used to determine the at least four controller output signals, at least two groups of acoustical transducers and a signal modifier for modifying, combining and directing controller output signals, either separately or in combination, to each group of acoustical transducers so as to provide an acoustic field conforming to a pre-determined specification.

Embodiments hereof also include a direct field acoustic testing system contained within an acoustic enclosure offering acoustic isolation from the surrounding environment and pre-determined reverberant characteristics with at least four microphones disposed in appropriate locations to provide at least four acoustical input signals which are used to determine the at least four controller output signals and at least four groups of acoustical transducers wherein said acoustic enclosure is portable.

Embodiments hereof also include a direct field acoustic testing system contained within an acoustic enclosure offering acoustic isolation from the surrounding environment and pre-determined reverberant characteristics with at least four microphones disposed in appropriate locations to provide at least four acoustical input signals which are used to determine the at least four controller output signals and at least two groups of acoustical transducers wherein said direct field acoustic testing system is pre-installed in said acoustic enclosure and said acoustic enclosure with pre-installed equipment is portable.

Embodiments hereof also include a direct field acoustic testing system contained within an acoustic enclosure offering acoustic isolation from the surrounding environment and pre-determined reverberant characteristics, at least four control microphones, a multiple-input-multiple-output (MIMO) vibration control system having at least four inputs and at least four separately controllable controller outputs, at least four separately driven groups of acoustical transducers and a signal modifier for modifying and directing separately controllable controller output signals, either separately or in combination, to each of the at least four separate groups of transducers so as to provide an acoustic field conforming to a pre-determined specification.

Embodiments hereof also include a direct field acoustic testing system contained within an acoustic enclosure offering acoustic isolation from the surrounding environment and pre-determined reverberant characteristics, at least four control microphones, a multiple-input-multiple-output (MIMO) vibration control system having at least four inputs and at least four separately controllable controller outputs, at least four separately driven groups of acoustical transducers and a signal modifier and combiner for modifying and directing combinations of controller output signals to each of the at least four groups of acoustical transducers wherein at least two of the separately controllable controller output signals are each directed to at least two groups of acoustical transducers in such a way as to provide an approximately even distribution of said at least two separately controllable controller output signals within the test environment so as to provide an acoustic field having a higher degree of spatial uniformity.

BRIEF DESCRIPTION OF THE DRAWINGS

Embodiments of the invention will now be described, by way of example only, with reference to the accompanying schematic drawings in which corresponding reference symbols indicate corresponding parts.

DETAILED DESCRIPTION OF EMBODIMENTS OF THE INVENTION

Figure 1:
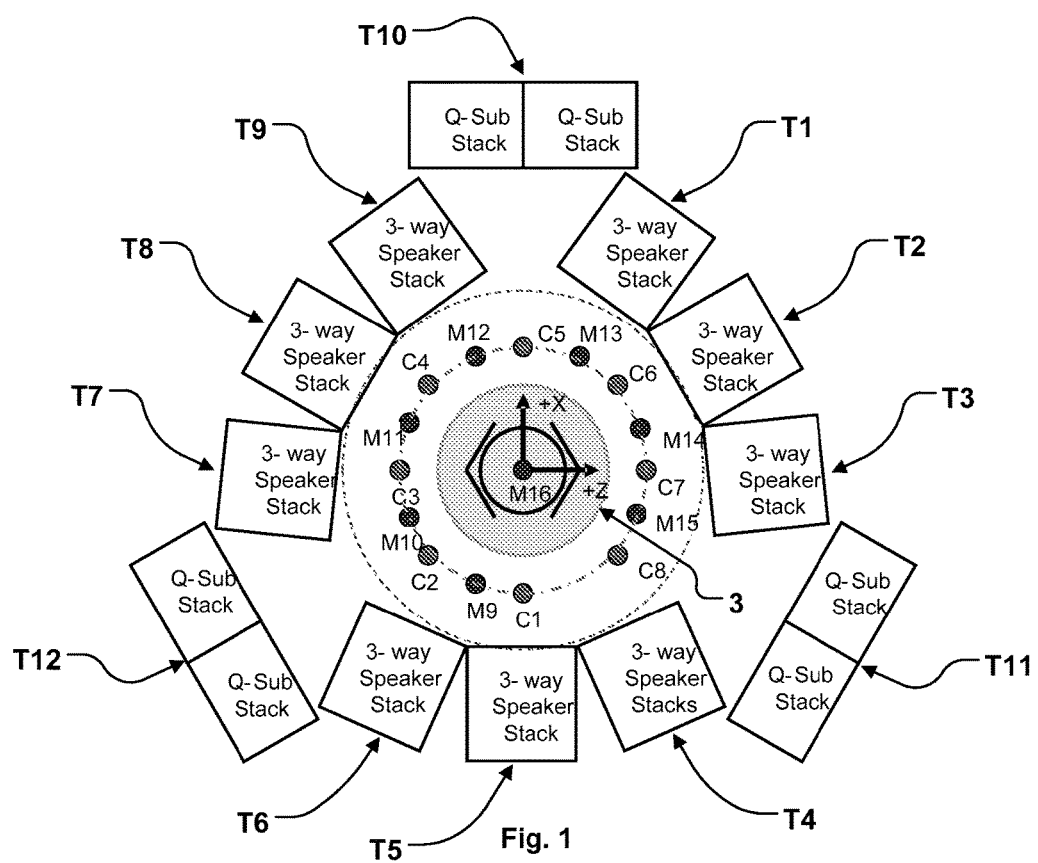
FIG. 1 schematic layout of an acoustical transducer group for direct field acoustic testing according to the '870 application.

Embodiments hereof are now described with reference to the figures in which like reference characters/numbers indicate identical or functionally similar elements. While specific configurations and arrangements are discussed, it should be understood that this is done for illustrative purposes only. A person skilled in the relevant art will recognize that other configurations and arrangements can be used without departing from the spirit and scope of the invention.

Referring to FIG. 1, an embodiment of a DFAT system in accordance with co-pending U.S. application Ser. No. 13/117,870, filed May 27, 2011 ("the '870 application) is shown. Included is a transducer array composed of electrodynamic acoustic sources or transducers T1-T12 covering various frequency ranges arrayed around the unit-under test (UUT) 3 in a generally circular arrangement as shown. The transducer array in the embodiment shown is composed of twelve groups T1-T12 of eight transducers, of which nine groups T1-T9 are three-way electro-dynamic loudspeaker systems generally covering the frequency range above 100 Hz and three groups T10-T12 are electro-dynamic subwoofer loudspeakers generally covering the frequency range from 20 Hz to 200 Hz. Control microphones C1-C12 are disposed at various positions around the UUT 3 for the purpose of providing information about the acoustic field to a control system (described below). Monitoring microphones M9-M16 may also be provided for monitoring the acoustic field at specific points of particular interest during operation but are not essential to the operation of this or any other embodiment hereof. Monitoring microphones may be located anywhere in the acoustic test space and need not correspond to control microphone locations.

Figure 2:
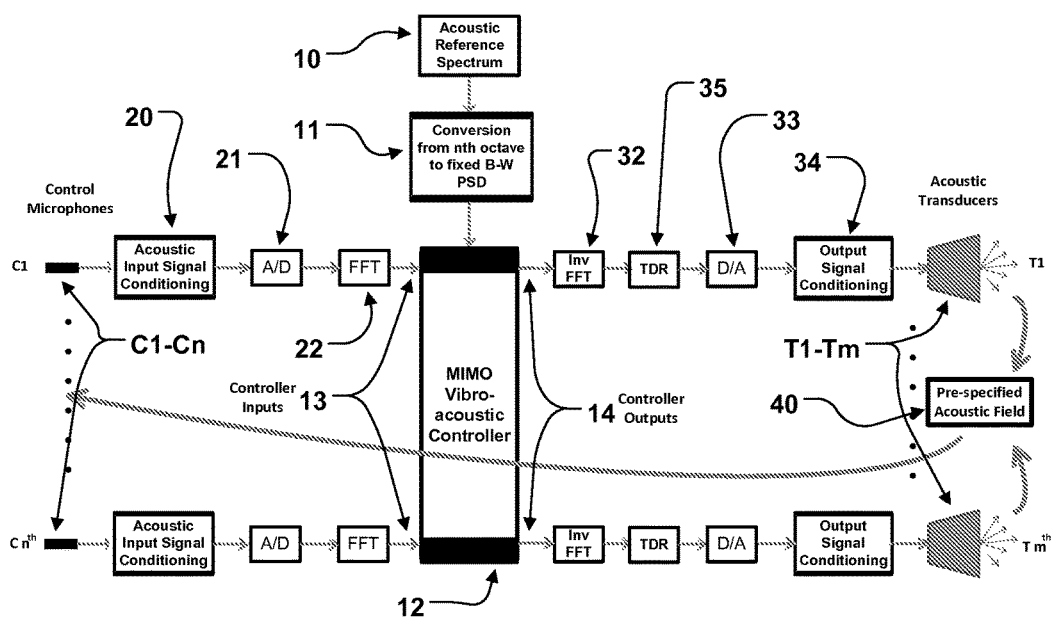
FIG. 2 is simplified block diagram of a direct field acoustic testing system according to the '870 application.

Referring to FIG. 2, a simplified block diagram of the DFAT system of FIG. 1 in accordance with the '870 application is shown. Each of the control microphones C1-Cn produces electrical signals which are representative of the acoustic field at each microphone. Each of the electrical signals is conditioned in an input signal conditioner 20 according to the input requirements of a vibro-acoustic controller 12. By way of example and not of limitation, conditioner 20 may include anti-aliasing or other filters, application of microphone calibration data referenced to appropriate standards, and scaling of the signal to represent the proper units. An analog to digital converter 21 converts the conditioned electrical signals to a digital format and the digitized signals are converted to fixed band-width narrow-band power spectral densities by application of a Fast Fourier Transform (FFT), as represented in block 22 of FIG. 2. Each of these resulting data streams is connected to one input 13 of the vibro-acoustic controller 12. Those of ordinary skill in the art recognize that the input signal conditioner 20, ND converter 21, and the FFT 22 may be part of the controller 12. Each output 14 from the controller 12 is converted from a narrow-band power spectral density to a digitized time series by an inverse FFT, as represented in block 32. This digitized time series may then be time domain randomized 35 depending on the type of test being conducted and then converted to an analog signal in digital to analog converter 33. Each analog signal is then conditioned in output signal conditioner 34 according to the input requirements of the amplification and acoustic transducers T1-Tm. By way of example and not of limitation, the conditioning may include additional filtering, gain, attenuation or power amplification. Each of the conditioned signals is then applied to the respective acoustical transducer group, T1-Tm. A pre-specified acoustical reference spectrum 10 is converted from the standard 1/nth octave format to a fixed band-width narrow-band power spectral density format which is consistent with the format of the signals from the control microphones C1-Cn and applied to the vibro-acoustic controller inputs 13. Those of ordinary skill in the art recognize that the inverse FFT 32, time domain randomization, the digital to analog converted 33, and the output signal conditioner may part of the controller 12.

Figure 3:
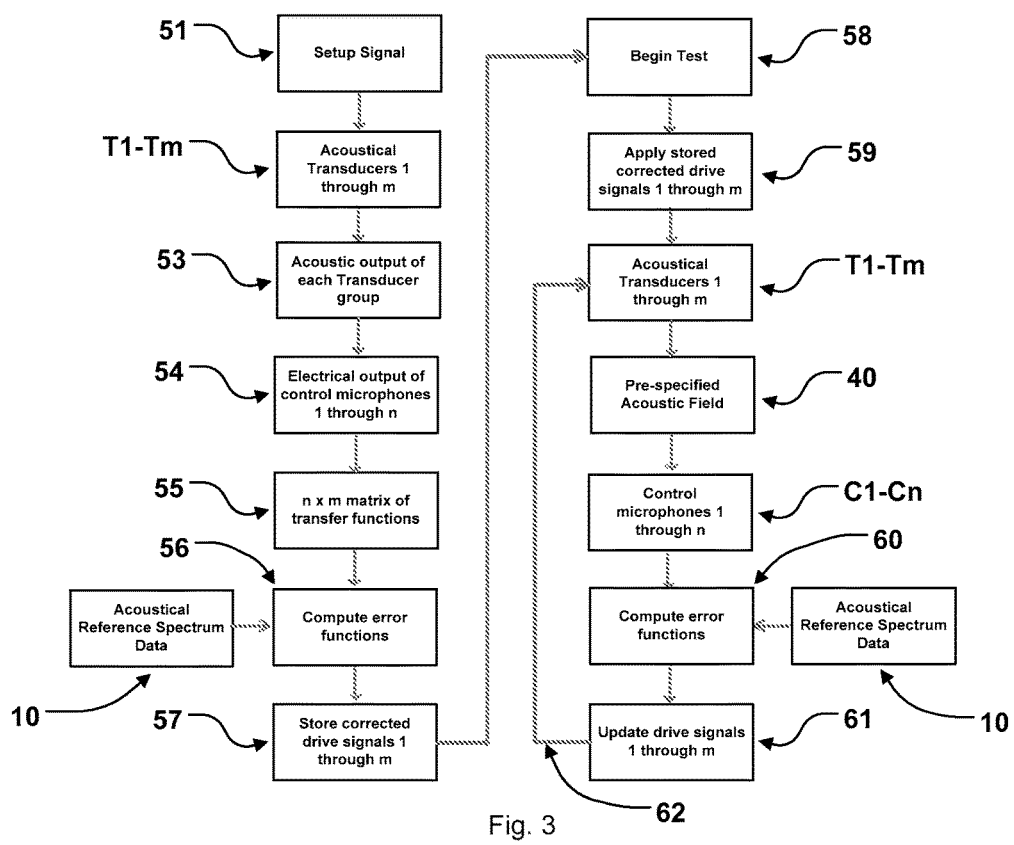
FIG. 3 is a simplified control diagram for the vibro-acoustic controller of the system of FIG. 2

The principles of multiple-input-multiple-output (MIMO) control logic will be familiar to those skilled in the art and may be applied in many different ways within the scope of the present invention in the implementation of this and other embodiments. Referring to FIG. 3, a simplified block diagram which describes generally the functioning of one possible embodiment of a MIMO vibro-acoustic controller 12 is shown which is in accordance with the '870 application. During the setup process a signal 51 is applied to each of the acoustical transducer groups T1-Tm. The acoustic output 53 of each transducer group is separately monitored by each control microphone C1-Cn. The electrical outputs of control microphones C1-Cn in response to each transducer group represent the transfer functions of each combination of transducer group and control microphone which are recorded in an n×m matrix 55 where each element is one such transfer function. These transfer functions are compared to the acoustical reference spectrum data 10. A matrix of error functions 56 is computed which is used to compute a corrected drive signal 57 for each of the transducer groups T1-Tm. At the start of the actual test 58 the previously stored 1 through m corrected drive signals 57 are applied 59 to the respective transducer groups T1-Tm. The resulting acoustic field is monitored by the control microphones C1-Cn and their outputs are compared to the acoustical reference spectrum data 10 from which error functions 60 are computed. These error functions 60 are used to provide real time updates of the drive signals 61 which are applied to through control loop 62 to the respective transducer groups T1-Tm. This embodiment may be operated in either closed loop control mode as shown in FIG. 3 or in open loop control mode. In open loop mode no real time adjustments to the drive signals are made after the initial application 59 of the stored corrected drive signals 57 computed during the setup process. Therefore the computation of error functions in block 60, the resulting update of drive signals 61 and feedback loop 62 would be omitted. Control microphones C1-Cn would therefore perform only a monitoring function.

Vibro-acoustic controller 12 may be any controller capable of performing the functions of the controller listed above. Controller 12 generally includes a processor and a graphical user interface (not shown), as known to those of ordinary skill in the art. In an embodiment, controller 12 may be an existing mechanical vibration controller such as, by way of example and not of limitation, the Spectral Dynamics Jaguar system.

In the embodiment shown and described with respect to FIGS. 1-3 there are n=12 control microphones C1-C12 and m=12 transducer groups T1-T12. However, those of ordinary skill in the art recognize that more or less control microphones and transducer groups may be utilized. For example, and not by way of limitation, the number of control microphones may be in the range of one to sixteen and the number of separately driven transducer groups may be in the range of four to sixteen. However, those of ordinary skill in the art recognize that additional control microphones and separately driven transducer groups may be utilized depending on the unit under test and the limits of controller 12. The band-width of the individual frequency bands of the power spectral density data used to represent the acoustical input signals and acoustical reference spectrum data is preferably equal to or less than 12.5 Hz and may be any suitable narrow band-width as determined by the characteristics of the available FFT functions such as and by way of example; 6.25 Hz, 3.125 Hz, 2.5 Hz, 1.25 Hz or 0.625 Hz. Such fixed band-width narrow-band frequencies have been shown to be important in controlling enclosure anomalies which are themselves typically narrow band in nature.

Figure 4:
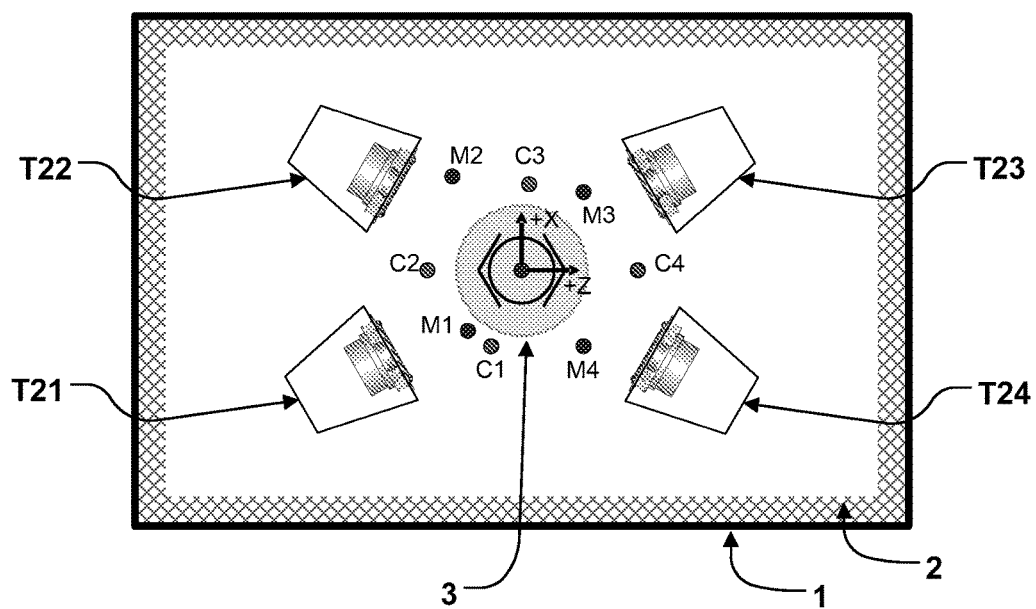
FIG. 4 is simplified layout of a direct field acoustic testing system in accordance with an embodiment hereof.

Referring to FIG. 4 there is shown a simplified layout of a semi-reverberant acoustic testing system in accordance with an embodiment hereof. Acoustic transducers T21-T24 perform functions similar to acoustic transducers T1-T12 of FIG. 1 except that each acoustic transducer T21-T24 covers the entire frequency range required by the test specification. Control microphones C1-C4 and monitor microphones M1-M4 also perform similar functions to microphones C1-C8 and M9-M15 of FIG. 1 and are arranged in the acoustic space between the acoustic transducers and the UUT, 3. Additionally, the acoustic transducers, microphones and UUT are contained within an enclosure 1 which completely encloses the acoustic test space, provides acoustic isolation from the surrounding environment and which has additional acoustic treatments 2 on its inner walls to control the reverberant characteristics of the enclosure 1. As a result of the increased proportion of reflected sounds in the area proximate to the UUT, less power is required to achieve a given acoustic test level than in a purely direct field acoustic test. However, in order to achieve a consistent and well controlled acoustic field at both control microphone locations C1-C4 and monitor microphone locations M1-M4 the reverberant behavior and other acoustic characteristics of the enclosure must be appropriately pre-determined through selection of dimensions, wall construction and acoustic treatment 2 of the walls. Additionally, the placement of the acoustic transducers M21-M24 must be chosen to achieve a desirable ratio of direct sound to reflected sound in the acoustic space surrounding the UUT.

In accordance with one embodiment hereof only four groups of acoustic transducers are required. However, it will be apparent to anyone skilled in the art that any number of acoustic transducers may be employed subject only to the physical size constraints of the enclosure. Additionally, a minimum of four control microphones are required but any number may be employed subject to the limitations of the controller inputs and other associated equipment.

In accordance with another embodiment hereof a minimum of four acoustic transducer groups are independently controlled in a Multiple-Input-Multiple-Output, MIMO control arrangement such as described in the co-pending '870 application. Experiments have shown that a larger number of control microphones and transducer groups may help to overcome excessive reverberant energy in the enclosure 1 or other flaws in the construction of the enclosure 1. Those of ordinary skill in the relevant art will recognize that more or less control microphones, monitor microphones and transducer groups may be utilized than are shown in the drawings subject only to the limitations of the controller 12 and the physical limitations of the acoustic enclosure 1.

Figure 5:
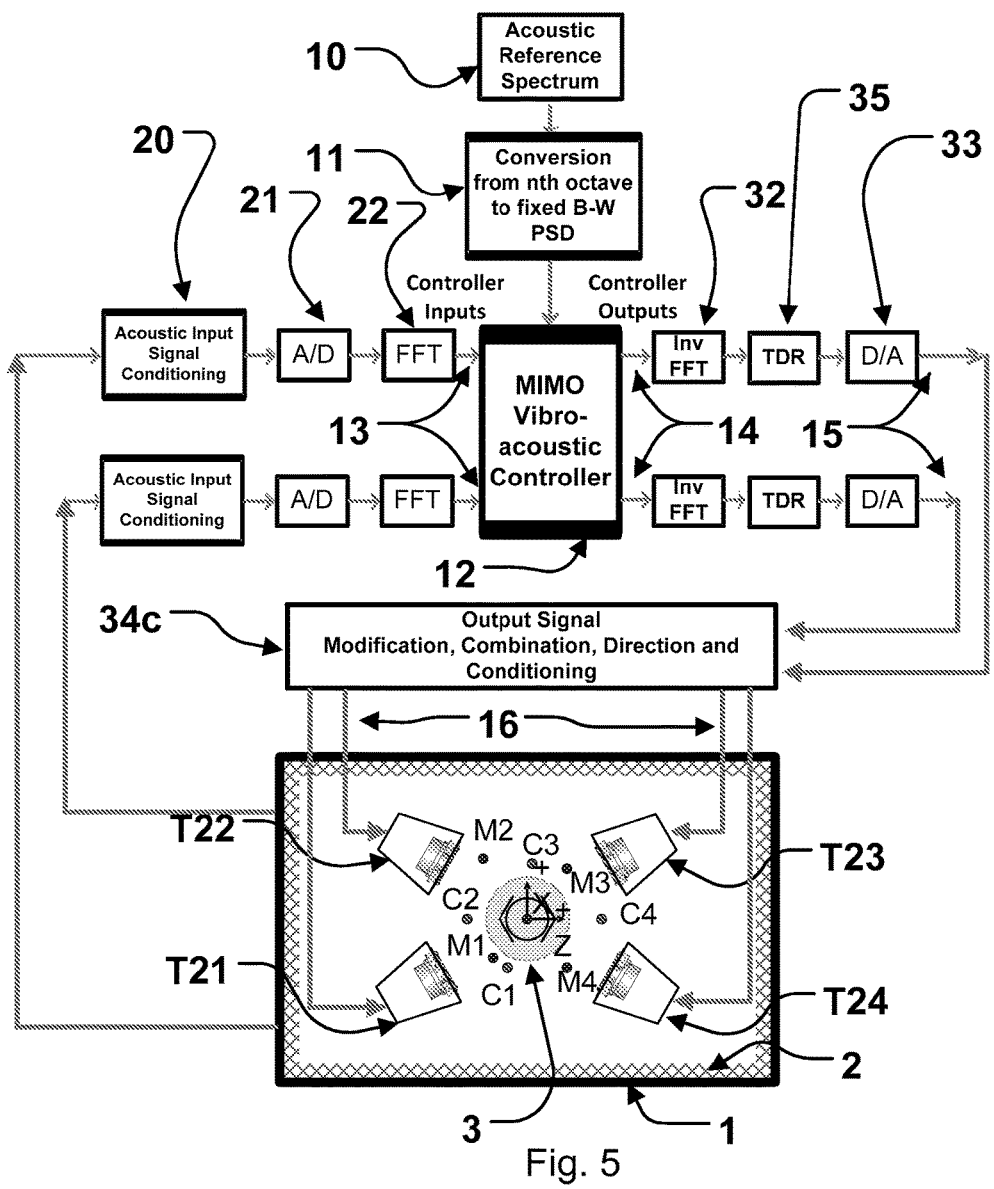
FIG. 5 is a simplified block diagram of semi-reverberant acoustic testing system in accordance with an embodiment hereof.

Referring to FIG. 5, there is shown a simplified block diagram in accordance with an embodiment hereof. Features are as described for FIG. 2 and are marked with the same reference numbers excepting that in FIG. 5 output signal conditioning means 34 of FIG. 2 has been replaced with output signal modification, combination, direction and conditioning means 34c and that acoustic transducers T21-24, control microphones C1-4 and monitor microphones M1-4 are contained with acoustic enclosure 1 as shown also in FIG. 4. After passing through digital to analog convertors 33 output signal modification, combination, direction and conditioning means 34c creates a secondary group of output signals 16 each of which is a combination of one or more of the controller output signals 15. The effect of the acoustic characteristics of the enclosure 1 are automatically accommodated in the setup process described previously with regard to FIG. 3. Those of ordinary skill in the relevant art will recognize that more or less control microphones, monitor microphones and transducer groups may be utilized than are shown in the drawings subject only to the limitations of the controller 12 and the physical limitations of the acoustic enclosure 1.

Output signal modification, combination, direction and conditioning means 34c creates a secondary each of which is a combination of one or more of the separately controllable controller output signals 15. Output signal modification, combination, direction, and conditioning means may also include an output signal conditioner to modifying each output signal according to the input requirements of the amplification and acoustical transducers T21-T24. By way of example and not of limitation, the conditioning may include additional filtering, gain, attenuation or power amplification. Each of the conditioned signals is then applied to the respective acoustical transducer group T21-T24. By way of example and not of limitation, output signal modification, combination, direction, and conditioning means 34*c* may create said secondary output signals 16 by attenuating, amplifying, filtering, delaying, adding, subtracting, correlating or any other manipulation of separately controllable controller output signals 15 so as to create appropriate combinations of signals for each group of transducers. Modification, combination, direction, and conditioning means 34*c* may be, for example and not by way of limitation, any suitable matrix switch or mixer or digital signal processor (DSP) unit such as the RANE RPM-88 or Yamaha DME64N. Additionally the modification, combination, direction and conditioning means 34*c* need not be a separate unit and may be in a different position in the signal path, as known to those skilled in the art. Output signal modification, combination, direction and conditioning means 34*c* may be as described in U.S. Provisional Application No. 61/552,081 and International Application No. PCT/US12/62255, both titled Drive Signal Distribution for Direct Field Acoustic Testing, each of which is incorporated by reference herein in its entirety. Such a signal output signal modification, combination, direction, and conditioning means 34*c* provides an approximately even distribution of the separately controllable controller output signals within the test environment so as to provide an acoustic field having a higher degree of spatial uniformity. Such spatial uniformity is especially important with testing taking place in an acoustic enclosure, as described herein.

Referring again to FIG. 4 it is often desirable that the test be performed at the current location of the UUT so as to avoid the risk and cost of shipment of the UUT. Therefore, in accordance with an embodiment hereof, the acoustic enclosure 1 is of a portable size and construction which will facilitate shipment or delivery to the test site. The acoustic enclosure may be in the form of a self contained shipping container or configured to fit into a truck or other vehicle dedicated to transport of the acoustic enclosure. Additional equipment such as the acoustic transducers T21-T24 and microphones C1-C4 and M1-M4 may or may not be installed during transport. In a specific implementation of this embodiment a standard 40 foot shipping container is used as the enclosure with exterior dimensions of approximately 40 feet in length, 8 feet in width, and 8.5 feet in height (approximate interior volume of 2385 cubic feet). In another specific implementation hereof a standard 20 foot shipping container is used as the enclosure with exterior dimensions of approximately 20 feet in length, 8 feet in width, and 8.5 feet in height (approximate interior volume of 1169 cubic feet). Those skilled in the art would recognize that changes in these dimensions, such as using "high-cube" containers, different sized containers (such as 45 foot high cube containers and 53 foot high cube containers with approximate internal volumes of 3040 cubic feet and 3857 cubic feet, respectively), "pallet-wide" containers used to accommodate standard European sized pallets, or other dimension variations may be used without departing from the spirit or scope of the invention.

As shown in FIG. 5 another specific implementation of an embodiment hereof is shown which includes an enclosure 1 with exterior dimensions of approximately 7 feet long, 5 feet high, 5 feet wide (approximate interior volume of 160 cubic feet), four control microphones C1-C4, a multiple-input-multiple-output (MIMO) vibration control system 12 with four inputs and four separately controllable controller outputs, four separately driven groups of acoustical transducers T21-T24 and a signal modifier 34*c* for modifying and directing separately controllable controller output signals, either separately or in combination, to each of the four separate groups of transducers so as to provide an acoustic field conforming to a pre-determined specification.

What is claimed is:

1. An acoustic testing system comprising:
   at least four control microphones;
   at least four acoustic transducers or groups of transducers;
   a portable acoustic enclosure with pre-determined reverberant characteristics, wherein said at least four control microphones and said at least four acoustic transducers or groups of transducers are pre-installed in said portable acoustic enclosure during transport of said portable acoustic enclosure via a truck; and
   a control system configured to produce a predetermined acoustic field as measured by said at least four control microphones,
   wherein the at least four acoustic transducers or groups of transducers are operatively coupled to the control system such that an output of each transducer is separately controllable by the control system such that a separate output signal is received by each transducer from the control system.

2. The acoustic testing system of claim 1, wherein said control system is operatively coupled to said at least four control microphones such that said control system receives at least one input signal from said at least four control microphones.

3. The acoustic testing system of claim 2, wherein said input signal is an averaged signal from said plurality of control microphones.

4. The acoustic testing system of claim 2, wherein said input signal comprises a separate input signal from each of said at least four control microphones.

5. The acoustic testing system of claim 1, wherein said portable acoustic enclosure includes an acoustic treatment on walls of said portable acoustic enclosure.

6. The acoustic testing system of claim 1, wherein said control system accounts for reflected sounds from said portable acoustic enclosure such that said predetermined acoustic field measured by said at least four control microphones is achieved with less power than said predetermined acoustic field without said portable acoustic enclosure.

7. The acoustic testing system of claim 1, wherein said control system is configured to compare an output signal of each of said at least four control microphones with respect to each acoustic transducer or group of transducers to a reference spectrum to create a matrix of error functions; and
   wherein said separate output signal received by each acoustic transducer or group of transducers is a corrected drive signal computed from the matrix of error functions.

8. The acoustic testing system of claim 7, wherein the reference spectrum is expressed as a fixed band-width narrow-band power spectral density.

9. The acoustic testing system of claim 8, wherein a band-width of the fixed band-width narrow band spectral density is less than or equal to 12.5 Hz.

10. The acoustic testing system of claim 1, wherein said portable acoustic enclosure is selected from the group consisting of a 20 foot shipping container, a 40 foot shipping container, a 45 foot high cube shipping container, a 53 foot high cube shipping container, and a 7 foot by 5 foot by 5 foot container.

11. The acoustic testing system of claim 1, wherein said portable acoustic enclosure has an internal volume of less than 4000 cubic feet.

12. The acoustic testing system of claim 1, wherein said portable acoustic enclosure has an internal volume of less than 3000 cubic feet.

13. A method of direct field acoustic testing of a unit under test comprising the steps of:
pre-installing at least four acoustic transducers and at least four control microphones within a portable acoustic enclosure with pre-determined reverberant characteristics;
transporting the portable acoustic enclosure with said pre-installed at least four acoustic transducers and said pre-installed at least four control microphones via a truck to a location of the unit under test;
positioning the unit under test within the portable acoustic enclosure such that the at least four acoustic transducers are disposed around the unit under test;
applying a setup signal to each of the acoustic transducers;
separately monitoring an acoustic output of each of the acoustic transducers using the at least four control microphones;
comparing an output signal of each of said at least four control microphones with respect to each of said at least four acoustic transducers to a reference spectrum to create a matrix of error functions;
computing a corrected drive signal for each of said at least for acoustic transducers; and
applying each corrected drive signal to the respective acoustic transducer.

14. The method of claim 13, wherein the output signal of the at least one control microphone is converted to a fixed band-width narrow band spectral density.

15. The method of claim 14, wherein the band-width of the fixed band-width narrow band spectral density is less than or equal to 12.5 Hz.

16. The method of claim 13, wherein the portable acoustic enclosure is selected from the group consisting of a 20 foot shipping container, a 40 foot shipping container, a 45 foot high cube shipping container, a 53 foot high cube shipping container, and a 7 foot by 5 foot by 5 foot container.

17. The method of claim 13, wherein the portable acoustic enclosure has an internal volume of less than 4000 cubic feet.

18. The method of claim 17, wherein the portable acoustic enclosure has an internal volume of less than 3000 cubic feet.

* * * * *